(12) United States Patent
Chen et al.

(10) Patent No.: US 11,180,440 B2
(45) Date of Patent: Nov. 23, 2021

(54) METHOD FOR PREPARING ISOPHORONE DIAMINE BY MEANS OF HYDROGENATION REDUCTION OF ISOPHORONE NITRILE IMINE

(71) Applicants: Zhejiang Nhu Company Ltd., Zhejiang (CN); Zhejiang University, Zhejiang (CN); Shandong Nhu Amino Acid Co., Ltd., Shandong (CN); Shandong Nhu Fine Chemical Science and Technology Company Ltd., Shandong (CN)

(72) Inventors: Zhirong Chen, Zhejiang (CN); Jianyong Mao, Shandong (CN); Baishan Hu, Zhejiang (CN); Guanbing Li, Zhejiang (CN); Haoran Li, Zhejiang (CN); Yu Wang, Zhejiang (CN); Yingkuo Yang, Zhejiang (CN); Qing Liu, Zhejiang (CN); Jiyu Tang, Shandong (CN); Weiyong Chen, Shandong (CN)

(73) Assignees: Zhejiang Nhu Company Ltd., Zhejiang (CN); Zhejiang University, Zhejiang (CN); Shandong Nhu Amino Acid Co., Ltd., Shandong (CN); Shandong Nhu Fine Chemical Science and Technology Company Ltd., Shandong (CN)

( * ) Notice: Subject to any disclaimer, the term of this patent is extended or adjusted under 35 U.S.C. 154(b) by 58 days.

(21) Appl. No.: 16/954,774

(22) PCT Filed: Nov. 30, 2018

(86) PCT No.: PCT/CN2018/118616
§ 371 (c)(1),
(2) Date: Jun. 17, 2020

(87) PCT Pub. No.: WO2019/120064
PCT Pub. Date: Jun. 27, 2019

(65) Prior Publication Data
US 2021/0087133 A1  Mar. 25, 2021

(30) Foreign Application Priority Data
Dec. 22, 2017 (CN) .......................... 201711408135.1

(51) Int. Cl.
*C07C 209/52* (2006.01)
*B01J 23/78* (2006.01)
(Continued)

(52) U.S. Cl.
CPC ............. *C07C 209/52* (2013.01); *B01J 23/78* (2013.01); *B01J 35/04* (2013.01); *C07C 209/48* (2013.01)

(58) Field of Classification Search
None
See application file for complete search history.

(56) References Cited

U.S. PATENT DOCUMENTS 3,352,913 A   11/1967   Schmitt et al.
5,395,972 A   3/1995    Furutani et al.
(Continued)

FOREIGN PATENT DOCUMENTS

CN     1561260 A     1/2005
CN     101260047 A   9/2008
(Continued)

OTHER PUBLICATIONS

Liu, Ying-Xin et al.; Synthesis of Isophorone Diamine and its Reaction Condition Optimization, with English abstract; Journal of Chemical Engineering of Chinese Universities; Jun. 2015; No. 3, vol. 29; pp. 616-620.
(Continued)

*Primary Examiner* — Sudhakar Katakam
*Assistant Examiner* — Jennifer C Sawyer
(74) *Attorney, Agent, or Firm* — Ulmer & Berne LLP

(57) ABSTRACT

The present disclosure relates to a method for preparing isophorone diamine by means of a hydrogenation reduction
(Continued)

of isophorone nitrile imine. The hydrogenation reduction is continuously carried out in a multi-stage bubble column reactor loaded with a supported alkaline cobalt-based catalyst, wherein isophorone nitrile imine is successively in countercurrent contact with hydrogen in each stage of the reactor to carry out a hydrogenation reduction reaction, so as to obtain the isophorone diamine. The preparation method solves the problem of back-mixing, and further improves the conversion rate and the cis/trans ratio of the product.

9 Claims, 1 Drawing Sheet

(51) Int. Cl.
*B01J 35/04* (2006.01)
*C07C 209/48* (2006.01)

(56) References Cited

U.S. PATENT DOCUMENTS

| | | |
|---|---|---|
| 5,583,260 A | 12/1996 | Haas et al. |
| 5,589,596 A | 12/1996 | Furutani et al. |
| 5,679,860 A * | 10/1997 | Haas .................... C07C 209/48 564/448 |
| 5,756,845 A | 5/1998 | Voit et al. |
| 2011/0313187 A1 | 12/2011 | Wigbers et al. |

FOREIGN PATENT DOCUMENTS

| | | |
|---|---|---|
| CN | 101386579 A | 3/2009 |
| CN | 101568516 A | 10/2009 |
| CN | 101768084 A | 7/2010 |
| CN | 102307660 A | 1/2012 |
| CN | 102531916 A | 7/2012 |
| CN | 102924291 A | 2/2013 |
| CN | 102976956 A | 3/2013 |
| CN | 103228614 A | 7/2013 |
| CN | 103265437 A | 8/2013 |
| CN | 103429563 A | 12/2013 |
| CN | 104119233 A | 10/2014 |
| CN | 104230721 A | 12/2014 |
| CN | 104370750 A | 2/2015 |
| CN | 105198755 A | 12/2015 |
| CN | 108017547 A | 5/2018 |
| EP | 0659733 A1 | 6/1995 |

OTHER PUBLICATIONS

State Intellectual Property Office of the P. R. China; International Search Report and Written Opinion of the International Searching Authority issued in International App. No. PCT/CN2018/118616; dated Feb. 19, 2019; 11 pages, including English translation of the International Search Report.

* cited by examiner

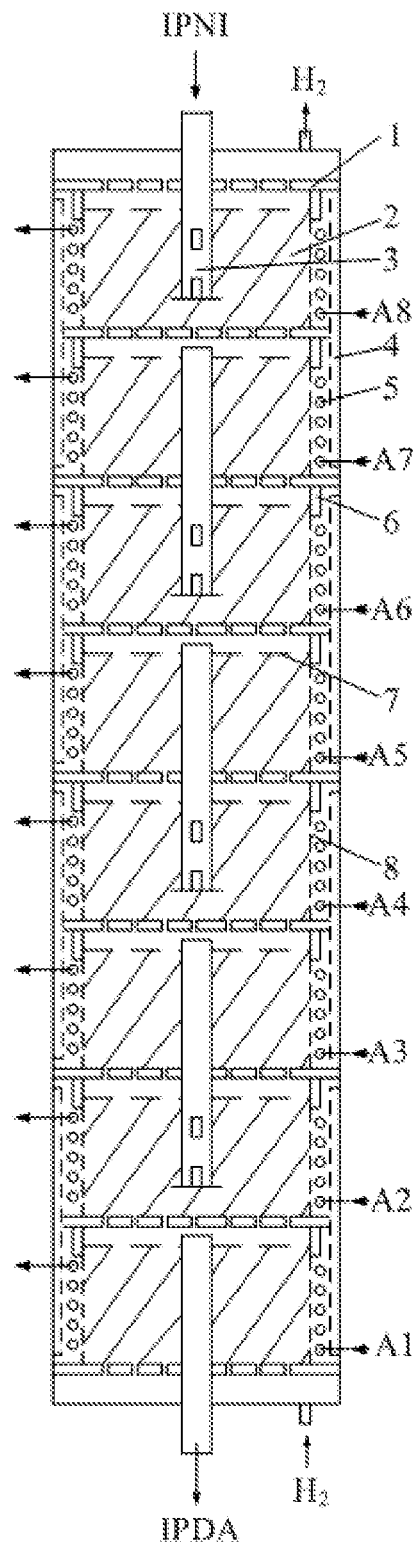

METHOD FOR PREPARING ISOPHORONE DIAMINE BY MEANS OF HYDROGENATION REDUCTION OF ISOPHORONE NITRILE IMINE

TECHNICAL FIELD

The present disclosure relates to the field of fine chemical industry, and in particular, a method for preparing isophorone diamine by means of hydrogenation reduction of isophorone nitrile imine.

BACKGROUND

Isophorone diamine (simply referred to as IPDA), has a scientific name of 3-aminomethyl-3,5,5-trimethylcyclohexylamine, a molecular formula of $C_{10}H_{22}N_2$ and a molecular weight of 170.3. IPDA is a colorless to pale yellow transparent liquid with slight ammonia odor. It has a cis-isomer and a trans-isomer, and the cis/trans isomer ratio of the commercially used IPDA is about 75/25. IPDA may be used as a curing agent or a crosslinking agent for epoxy resin coatings. It may also be used to prepare the corresponding diisocyanate, i.e., isophorone diisocyanate (simply referred to as IPDI), and may be used to produce polyurethane and act as a crosslinking agent, a coupling agent, a hydroxyl stabilizer and a special monomer in the production of polyurethane.

IPDA is generally prepared by reacting 3-cyano-3,5,5-trimethylcyclohexanone (commonly known as isophorone nitrile, and simply referred to as IPN) with ammonia to form 3-cyano-3,5,5-trimethylcyclohexylimine (commonly known as isophorone nitrile imine, and simply referred to as IPNI), and subsequently subjecting IPNI and hydrogen to a reduction reaction. In the initial stage of the reduction reaction, a low temperature is conducive to the formation of IPDA having a high cis/trans isomer ratio. Among them, the imidization reaction of IPN generally uses methanol as a solvent and IPNI is generated under the action of a catalyst. The technique of generating IPNI by the imidization of IPN is mature, but currently reported reduction reactions of IPNI have problems about high reaction pressure, complicated operation, difficulty in the separation of by-products, etc.

The literature reports on the reduction reaction of IPNI may be divided into three categories based on different reaction modes: batch-wise reaction, continuous trickle bed reaction, and continuous bubbling bed reaction.

Among them, the literature reports on employing the batch-wise reaction are as below.

In U.S. Pat. No. 3,352,913, a batch-wise reaction is employed to prepare IPDA, and its process is as follows. IPN, ammonia and hydrogen are charged into a reaction kettle, and heated at 120° C. under a pressure of 15 MPa to react for 2 hours. An IPDA yield of 81.4% may be obtained, but the cis/trans ratio of the product is not mentioned. As compared with other patents, although this method has a reduced pressure, the IPDA yield is low along with many by-products.

Chinese patent CN101768084A prepares IPDA by subjecting IPN, ammonia and an aqueous formic acid solution to a reduction reaction at 150° C. in a batch reactor. Despite this method is simple and convenient and does not require the addition of other catalysts, it has low selectivity, and the gas phase content of IPDA in the resulting reaction liquid is only between 45% and 75%. The cis/trans ratio of the product is not mentioned.

Chinese patent CN101386579A prepares IPDA by reacting IPN, ammonia, an alcohol or ether solvent, a hydrogenation catalyst and a co-catalyst in a batch autoclave or a fixed bed at 50° C. to 120° C. under a hydrogen pressure of 5 to 15 MPa. The maximum gas phase content of IPDA in the final resulting reaction liquid is 96.5%, and the cis/trans isomer ratio of the product is between 73/27 and 82/18. However, an organic base or an inorganic base as a co-catalyst is required to be added in the reaction process.

All of the above literature reports adopt a batch reactor for operation. Their common problem is that each batch of production requires auxiliary operation processes such as loading, heating, unloading, and cleaning. Therefore, the production efficiency is low and the quality is difficult to control.

The literature reports on employing the continuous trickle bed reaction are as below.

Chinese patent CN1561260A employs a continuous trickle bed reactor and the hydrogenation reaction is carried out in three stages, wherein the reaction temperature in the first stage is 90° C., the reaction temperature in the third stage is 130° C., and the reaction process is carried out under a pressure of 250 bar. The IPDA product obtained by this method has a cis/trans ratio of 75.8/24.2, and has a yield of 92.5%.

Chinese patent CN101260047A introduces a preparation method for IPDA and employs a reactor for imidization and a reactor for hydrogenation reduction, wherein the hydrogenation reduction reaction is carried out in a trickle bed reactor, the temperature of the imidization reaction is 50° C., and the temperature in the reactor for hydrogenation reduction is 100° C., and the pressure is controlled at 252 bar. The maximum content of the product obtained in the Examples is 98.7%, but the cis/trans ratio of the product is not mentioned.

Chinese patent CN101568516A discloses a manufacturing method of IPDA. IPDA is prepared by subjecting IPNI resulting from the imidization of IPN, hydrogen and ammonia to a reduction reaction in a trickle bed reactor charged with a catalyst for hydrogenation reduction. This method is characterized in that the basicity of the reaction mixture is increased during the reaction by bringing the reaction mixture into contact with a basic compound (not ammonia) or a basic catalyst after part of IPNI has been reacted. In the final reaction liquid obtained from this method, the selectivity for IPDA is 93.4%, and the cis/trans isomer ratio of the product is 85/15.

Chinese patent CN102924291A introduces a method of synthesizing IPDA by hydrogenation reduction in a multi-stage trickle bed reactor. In the reduction process, in addition to the addition of a corresponding hydrogenation catalyst, an alkaline compound is introduced prior to the starting of the second-stage reaction, and an acidic compound is introduced prior to the third-stage reaction (namely, the last stage reaction), so as to facilitate the hydrogenation reaction. The content of IPDA in the Examples reaches 97.6% to 99%, but the cis/trans ratio of the product is not mentioned. Due to the introduction of two auxiliary agents during the reaction process, the reaction operation becomes complicated. Meanwhile, it also brings the problem of the treatment of waste water and waste salts, which increases the post-processing cost.

Chinese patent CN102976956A employs the following method. The reaction liquid resulting from the imidization of the raw material IPN is adsorbed, extracted or distilled to remove water, and then subjected to hydrogenation reduction reaction in a trickle bed. The hydrogenation reduction reaction is carried out under the conditions of 20° C. to 200° C. and 10 to 30 MPa. In its Examples, the yield of the product IPDA is 97.84% to 98.5%, and the cis/trans ratio of the product is not mentioned. This method adds a step of dehydrating an intermediate, which complicates the operation process. Regardless of which of the three operation modes described above, material loss or increased energy consumption will occur inevitably, thereby increasing the production cost.

Chinese patent CN103429563A also employs a trickle bed reactor, and the hydrogenation reduction reaction is carried out at 25° C. to 300° C. under a pressure of 0.1 to 20 MPa. The cross-sectional load of the reactor is 5 to 50 kg/m$^2$/s. By increasing the recirculation flow and thus increasing the cross-sectional load, the proportion of the intermediate IPAN is reduced from 24% at 4.2 kg/m$^2$/s to 7% at 15.8 kg/m$^2$/s, while the proportion of IPDA increases accordingly. The Examples do not mention the content of IPDA in the final reaction liquid and the cis/trans ratio of the product.

In Chinese patent CN104230721A, IPDA is prepared by carrying out a hydrogenation reduction reaction using a multistage trickle bed reactor. Its process is as follows. First, the resulting imidized reaction liquid and a circulating material are subjected to a first-stage hydrogenation reaction together to obtain a first hydrogenation reaction material, and then a second-stage hydrogenation reaction is carried out under the action of a heat-decomposable alkaline auxiliary agent, followed by decomposing the alkaline auxiliary agent by heating. A part of material after the decomposition reaction is recycled as the circulating material to the first-stage hydrogenation reaction and acts as an auxiliary agent, and the remaining part is subjected to the third-stage reaction. In the Examples, the reaction temperature is 40° C. to 150° C., the pressure is 16 MPa, the content of the product in the final resulting reaction liquid is 98%, and the cis/trans ratio of the product is not mentioned. This method introduces an auxiliary agent during the reaction process, and requires the recycling of the materials, thereby complicating the reaction operation.

In Chinese patent CN104370750A, the hydrogenation reduction reaction is carried out using a trickle bed reactor. In this method, there is a need for the addition of an alkaline regulator to the reaction liquid of the imidized IPN. The reaction temperature is controlled at 20° C. to 80° C., and the pressure is preferably 15 to 20 MPa. The highest IPDA content obtained in the Examples is 98.75%, and the cis/trans ratio of the product is not mentioned. Since an alkaline regulator needs to be added during the reaction, the post-processing operation of the reaction liquid may be increased and waste water and waste salts are brought about.

The hydrogenation reduction reactions reported in the above literatures all employ a trickle bed reactor, and the hydrogenation reduction reactions are strong exothermic reactions, therefore, it is liable to generate hot spots in the early stage of the reaction, which is not conducive to obtaining a high cis/trans isomer ratio of the product.

In addition, there are several documents mentioning that either a trickle bed or a bubbling bed may be used as a hydrogenation reduction reactor.

In Chinese patents CN102531916A and CN105198755A, the reaction is carried out in a fixed bed operated in a trickle mode or in a bubbling bed operated in a bottom feeding mode, the reaction temperature is 20° C. to 150° C. and the reaction pressure is 0.3 to 50 MPa, and a cyanide solution, from which cyanide ions with a concentration of 1000 ppmw to 3000 ppmw are capable of being dissociated, is added.

Although this method reduces the content of the by-product bicyclic amine and its intermediate amidine, it also causes an increase in the content of the intermediate IPAN at the same time. The total yield of IPDA obtained in the Examples is 94.62% to 95.69%, and the cis/trans ratio of the product is not mentioned. The cyanide solution added in this method leads to a problem of cyanide-containing wastewater and increases the post-processing cost.

Chinese patent CN104119233A adopts two-stage hydrogenation, and the reactor is a bubbling bed or a trickle bed. In this method, after the hydrogenation in a first-stage hydrogenation reactor, deamination is carried out prior to the supplementary addition of a solvent, and a second-stage hydrogenation reaction is then carried out. The hydrogenation temperature is 100° C. to 130° C. and the pressure is within 10 MPa. The Examples show that the content of the obtained product IPDA may be 95.07% to 96.03%, and the cis/trans ratio of the product is not mentioned. Although this method may be carried out at a lower pressure, an ammonia removal device needs to be added and a supplementary addition of the solvent is needed in the two-stage hydrogenation process, which complicates the operation process and increases energy consumption.

The reactor employed in Chinese patent CN103228614A is a trickle bed or a bubbling bed operated in a bottom feeding mode. HCN or cyanide salt(s) needs to be added to the imidized reaction liquid to increase the concentration of the cyanide ion to 200 ppmw to 5000 ppmw. In this method, the hydrogenation reaction is carried out at 20° C. to 150° C. under a pressure of 0.3 to 50 MPa. The content of the product IPDA obtained in the Examples is 94.62% to 95.69%, and the cis/trans ratio of the product is not mentioned. Although as described in the patent, this method reduces the content of the by-product bicyclic amine and its intermediate amidine, the added cyanide solution also results in a problem of cyanide-containing waste water and increases the post-processing cost.

The bubbling bed reactor used in the above literatures has a problem of back-mixing, which is not conducive to improving the conversion rate, and the single-stage bubbling bed reactor also has a problem about hot spots.

SUMMARY

In view of the deficiencies of the prior art, an object of the present disclosure is to provide a method for preparing isophorone diamine by means of hydrogenation reduction of isophorone nitrile imine, which solves the problem of back-mixing and further increases the conversion rate and the cis/trans ratio of the product.

The technical solution provided by the present disclosure is as follows.

Provided is a method for preparing isophorone diamine by means of hydrogenation reduction of isophorone nitrile imine, wherein the hydrogenation reduction is carried out continuously in a multistage bubble column reactor loaded with a supported alkaline cobalt-based catalyst, and isophorone nitrile imine comes sequentially in countercurrent contact with hydrogen in each stage reactor to carry out a hydrogenation reduction reaction, thereby obtaining isophorone diamine.

The multistage bubble column reactor in the present disclosure is composed of multiple stage reactors connected in series. The raw material isophorone nitrile imine is continuously charged from the top during the hydrogenation reduction, and hydrogen is continuously introduced from the bottom. The reaction temperature in each stage reactor is controlled as required by the heat-exchanging medium in the heat-exchanging coil pipe in the stage reactor, and the product (a reaction liquid containing isophorone diamine) is obtained from the outlet at the bottom of the reactor.

The raw material isophorone nitrile imine in the present disclosure is obtainable from the preparation methods in the prior art, for example, the imidization of isophorone nitrile. An intermediate substance obtained after the hydrogenation reduction of isophorone nitrile imine via the first stage reactor and before the generation of the final product is referred to as the reaction liquid in the present disclosure. The reaction liquid comprises isophorone nitrile imine, isophorone diamine and a trace amount of by-product(s). With the increase of the number of stage reactors passed through by the reaction liquid, the content of isophorone diamine in the reaction liquid gradually increases, and a product with a high content is finally obtained.

Preferably, the multistage bubble column reactor includes 6 to 12 stage reactors.

Preferably, a sieve plate is used for separation between each stage reactor of the multistage bubble column reactor. By arranging pores on the sieve plate, hydrogen may be redistributed multiple times, which effectively increases the gas-liquid contact area between the reaction liquid and hydrogen and prevents the coalescence phenomenon of bubbles which is liable to occur in a single-stage reactor, thereby accelerating the speed of the main reaction and reducing the formation of by-products.

Preferably, the pores on the sieve plate only enable hydrogen to pass while not allowing the reaction liquid to pass, and the reaction liquid enters the next stage reactor through a downcomer pipe and a downcomer ring. Providing the downcomer pipe and the downcomer ring is able to not only solve the problem of back-mixing existing in the single-stage bubbling bed, but also control the flow range of the reaction liquid and increase the utilization rate of the catalyst as well as the conversion rate and selectivity of the reaction.

Preferably, the supported alkaline cobalt-based catalyst is separately provided in each stage reactor, and is fixed by using a sieve plate, a pressing plate and a dead plate; and the pores of the pressing plate and the dead plate enable hydrogen and the reaction liquid to pass.

Preferably, the supported alkaline cobalt-based catalyst comprises a carrier, an active component, and an alkaline component; the carrier includes one or more of alumina, titania, zirconium dioxide, and magnesia; the active component is Co; and the alkaline component includes an oxide of Mg, Ca, Na or K. Because of the use of the supported alkaline cobalt-based catalyst, other alkaline auxiliary agents are no longer needed to be added during the reaction process, and thus, no additional waste brine is generated, and the environmental pollution is reduced.

Preferably, the active component has a mass fraction of 30% to 50%; and the alkaline component has a mass fraction of 0.1% to 5%.

Preferably, the isophorone nitrile imine, when added as a reaction material, has a mass fraction of 97% or more.

Preferably, a molar ratio of hydrogen to isophorone nitrile imine is 5 to 100:1 during the hydrogenation reduction reaction; and a space-time processing capacity of catalyst of the multistage bubble column reactor is 0.05 to 0.3 mol/(L*h).

Preferably, the reaction temperature in the multistage bubble column reactor is 60° C. to 160° C., and the temperatures in adjacent reactors are the same or increase successively; and the reaction pressure in the multistage bubble column reactor is 3 to 10 MPa. It is further preferred that the temperature difference between adjacent reactors is 0° C. to 10° C., and the temperature shows a tendency of rise from the top of the column to the bottom of the column. The heat-exchanging coil pipe is capable of controlling the reaction temperature of each stage reactor according to the need of the reaction, which is beneficial to the formation of the temperature distribution required for a high cis/trans isomer ratio of IPDA.

Compared with the prior art, the present disclosure achieves the following beneficial effects. The process of synthesizing IPDA by hydrogenation reduction in a multistage bubble column reactor employed in the present disclosure has the advantages of a high conversion rate, high selectivity, a high cis/trans isomer ratio and easy amplification, and has a high industrial application value.

BRIEF DESCRIPTION OF THE DRAWINGS

FIG. 1 is a schematic diagram of the multistage bubble column reactor used in Example 1.

1. sieve plate; 2. catalyst; 3. downcomer pipe; 4. downcomer ring; 5. heat-exchanging coil pipe; 6. spacer ring; 7. pressing plate; 8. dead plate; A1 to A8 represent different stage reactors, respectively.

DETAILED DESCRIPTION

The present disclosure will be illustrated in detail below with reference to the accompanying drawing and the specific embodiments of the specification.

EXAMPLE 1

FIG. 1 showed an 8-stage continuous bubble column reactor. The column body was composed of stage reactors A1 to A8. A sieve plate 1 was used for separation between each stage reactor. The pores of the sieve plate 1 only enabled hydrogen to pass, while neither a reaction liquid nor a catalyst could pass. Each of the stage reactors A1 to A8 was loaded with a catalyst 2, and the catalyst 2 was fixed by a sieve plate 1, a pressing plate 7, and a dead plate 8. The pores of the pressing plate 7 and the dead plate 8 only enabled hydrogen and the reaction liquid to pass.

A heat-exchanging coil pipe 5 was also installed on the side which was close to the outer walls of the stage reactors A1 to A8, and a heat-exchanging medium in the heat-exchanging coil pipe 5 was used for stage-wise heating. In addition, a spacer ring 6 was also installed between the sieve plate 1 and the dead plate 8. A downcomer pipe 3 and a downcomer ring 4 were also installed between the stage reactors to control the flow range of the reaction liquid.

In the continuous bubble column reactor as described above, the volume of the catalyst in each stage reactor was 1 L, and the continuous bubble column reactor was loaded with a supported alkaline cobalt-based catalyst, in which the content of cobalt was 40%, the content of sodium oxide was 2%, and the carrier was alumina. Thereafter, an IPNI solution in which IPNI was the reactant having a content of 98.6% (except for the solvent) was added at 0.4 mol/h via a metering pump from the top of the bubble column, while hydrogen was consecutively introduced at 4 mol/h from the bottom. The space-time processing capacity of catalyst corresponding to this operating condition was 0.05 mol/(L*h), and the molar ratio of hydrogen to IPNI was 10. Hot oils with different temperatures were respectively introduced into the heat-exchanging coil pipes of A1 to A8, the temperatures of the stage reactors were respectively controlled at 60° C., 60° C., 70° C., 70° C., 80° C., 90° C., 100° C., and 110° C. from top to bottom, and the pressure was controlled at 3 MPa. The reaction product was collected from the bottom.

After the system was operated stably for 100 hours, the product was sampled and analyzed. The sampling analysis indicated that, in addition to ammonia and water, the reaction output contained the product IPDA with a content of 98.52% and the following main by-products according to the gas chromatography analysis. Among said main by-products, the content of 1,3,3-trimethyl-6-azabicyclo[3.2.1]octane (TAO) was 0.53%, the content of 1,3,3-trimethyl-6-azabicyclo[3.2.1]oct-7-ylideneamine (amidine) was 0.41%, and the content of 3-aminomethyl-3,5,5-trimethylcyclohexanol (IPAA) was 0.26%. The selectivity for IPDA was 98.5%, and the cis/trans isomer ratio was 83/17.

EXAMPLE 2

An 8-stage bubble column reactor as shown in FIG. 1 was used, and was loaded with a supported alkaline cobalt-based catalyst, in which the content of cobalt was 50%, the content of magnesium oxide was 5%, and the carrier was titanium dioxide. Thereafter, an IPNI solution in which IPNI was the reactant having a content of 97.2% (except for the solvent) was added at 2.4 mol/h via a metering pump from the top of the bubble column, while hydrogen was consecutively introduced at 240 mol/h from the bottom. The space-time processing capacity of catalyst corresponding to this operating condition was 0.3 mol/(L*h), and the molar ratio of hydrogen to IPNI was 100. Hot oils with different temperatures were respectively introduced into the heat-exchanging coil pipes of A1 to A8, the temperatures of the stage reactors were respectively controlled at 80° C., 80° C., 90° C., 90° C. 100° C., 120° C., 140° C., and 160° C. from top to bottom, and the pressure was controlled at 10 MPa. The reaction product was collected from the bottom.

After the system was operated stably for 60 hours, the product was sampled and analyzed. The sampling analysis indicated that, in addition to ammonia and water, the reaction output contained the product IPDA with a content of 98.31% and the following main by-products according to the gas chromatography analysis. Among said main by-products, the content of 1,3,3-trimethyl-6-azabicyclo[3.2.1]octane (TAO) was 0.62%, the content of 1,3,3-trimethyl-6-azabicyclo[3.2.1]oct-7-ylideneamine (amidine) was 0.45%, and the content of 3-aminomethyl-3,5,5-trimethylcyclohexanol (IPAA) was 0.28%. The selectivity for IPDA was 98.3%, and the cis/trans isomer ratio was 79/21.

EXAMPLE 3

An 8-stage bubble column reactor as shown in FIG. 1 was used, and was loaded with a supported alkaline cobalt-based catalyst, in which the content of cobalt was 30%, the content of potassium oxide was 0.1%, and the carrier was magnesium oxide. Thereafter, an IPNI solution in which IPNI was the reactant having a content of 98.2% (except for the solvent) was added at 1.2 mol/h via a metering pump from the top of the bubble column, while hydrogen was consecutively introduced at 24 mol/h from the bottom. The space-time processing capacity of catalyst corresponding to this operating condition was 0.15 mol/(L*h), and the molar ratio of hydrogen to IPNI was 20. Hot oils with different temperatures were respectively introduced into the heat-exchanging coil pipes of A1 to A8, the temperatures of the stage reactors were respectively controlled at 70° C., 70° C., 80° C., 90° C. 100° C., 110° C., 120° C. and 130° C. from top to bottom, and the pressure was controlled at 6 MPa. The reaction product was collected from the bottom.

After the system was operated stably for 80 hours, the product was sampled and analyzed. The sampling analysis indicated that, in addition to ammonia and water, the reaction output contained the product IPDA with a content of 98.42% and the following main by-products according to the gas chromatography analysis. Among said main by-products, the content of 1,3,3-trimethyl-6-azabicyclo[3.2.1]octane (TAO) was 0.57%, the content of 1,3,3-trimethyl-6-azabicyclo[3.2.1]oct-7-ylideneamine (amidine) was 0.40%, and the content of 3-aminomethyl-3,5,5-trimethylcyclohexanol (IPAA) was 0.27%. The selectivity for IPDA was 98.4%, and the cis/trans isomer ratio was 81/19.

EXAMPLE 4

An 8-stage bubble column reactor as shown in FIG. 1 was used, in which the number of stages was changed to 6, and the bubble column reactor was loaded with a supported alkaline cobalt-based catalyst, in which the content of cobalt was 30%, the content of potassium oxide was 0.1%, and the carrier was magnesium oxide. Thereafter, an IPNI solution in which IPNI was the reactant having a content of 98.2% (except for the solvent) was added at 0.9 mol/h via a metering pump from the top of the bubble column, while hydrogen was consecutively introduced at 27 mol/h from the bottom. The space-time processing capacity of catalyst corresponding to this operating condition was 0.15 mol/(L*h), and the molar ratio of hydrogen to IPNI was 30. Hot oils with different temperatures were respectively introduced into the heat-exchanging coil pipes of A1 to A6, the temperatures of the stage reactors were respectively controlled at 80° C., 90° C., 100° C., 110° C., 120° C. and 130° C. from top to bottom, and the pressure was controlled at 6 MPa. The reaction product was collected from the bottom.

After the system was operated stably for 70 hours, the product was sampled and analyzed. The sampling analysis indicated that, in addition to ammonia and water, the reaction output contained the product IPDA with a content of 98.13% and the following main by-products according to the gas chromatography analysis. Among said main by-products, the content of 1,3,3-trimethyl-6-azabicyclo[3.2.1]octane (TAO) was 0.59%, the content of 1,3,3-trimethyl-6-azabicyclo[3.2.1]oct-7-ylideneamine (amidine) was 0.46%, and the content of 3-aminomethyl-3,5,5-trimethylcyclohexanol (IPAA) was 0.31%. The selectivity for IPDA was 98.1%, and the cis/trans isomer ratio was 80/20.

EXAMPLE 5

An 8-stage bubble column reactor as shown in FIG. 1 was used, in which the number of stages was changed to 12, and the bubble column reactor was loaded with a supported alkaline cobalt-based catalyst, in which the content of cobalt was 40%, the content of calcium oxide was 2%, and the carrier was zirconium dioxide. Thereafter, an IPNI solution in which IPNI was the reactant having a content of 98.2% (except for the solvent) was added at 2.4 mol/h via a metering pump from the top of the bubble column, while hydrogen was consecutively introduced at 120 mol/h from the bottom. The space-time processing capacity of catalyst corresponding to this operating condition was 0.2 mol/(L*h), and the molar ratio of hydrogen to IPNI was 50. Hot oils with different temperatures were respectively introduced into the heat-exchanging coil pipes of A1 to A12, the temperatures of the stage reactors were respectively controlled at 70° C., 70° C., 80° C., 80° C., 90° C., 90° C., 100° C., 100° C., 110° C., 110° C., 120° C. and 120° C. from top to bottom, and the pressure was controlled at 8 MPa. The reaction product was collected from the bottom.

After the system was operated stably for 80 hours, the product was sampled and analyzed. The sampling analysis indicated that, in addition to ammonia and water, the reaction output contained the product IPDA with a content of 98.69% and the following main by-products according to the gas chromatography analysis. Among said main by-products, the content of 1,3,3-trimethyl-6-azabicyclo[3.2.1]octane (TAO) was 0.49%, the content of 1,3,3-trimethyl-6-azabicyclo[3.2.1]oct-7-ylideneamine (amidine) was 0.36%, and the content of 3-aminomethyl-3,5,5-trimethylcyclohexanol (IPAA) was 0.25%. The selectivity for IPDA was 98.7%, and the cis/trans isomer ratio was 82/18.

What is claimed is:

1. A method for preparing isophorone diamine by means of hydrogenation reduction of isophorone nitrile imine, wherein the hydrogenation reduction is carried out continuously in a multistage bubble column reactor loaded with a supported alkaline cobalt-based catalyst, and isophorone nitrile imine comes sequentially in countercurrent contact with hydrogen in each stage reactor to carry out a hydrogenation reduction reaction, thereby obtaining isophorone diamine, wherein the multistage bubble column reactor includes 6 to 12 stage reactors.

2. The method for preparing isophorone diamine by means of hydrogenation reduction of isophorone nitrile imine according to claim 1, wherein a sieve plate is used for separation between each stage reactor of the multistage bubble column reactor.

3. The method for preparing isophorone diamine by means of hydrogenation reduction of isophorone nitrile imine according to claim 2, wherein pores on the sieve plate only enable hydrogen to pass while not allowing a reaction liquid to pass, and the reaction liquid enters the next stage reactor through a downcomer pipe and a downcomer ring.

4. The method for preparing isophorone diamine by means of hydrogenation reduction of isophorone nitrile imine according to claim 2, wherein the supported alkaline cobalt-based catalyst is separately provided in each stage reactor, and is fixed by using the sieve plate, a pressing plate, and a dead plate; and pores of the pressing plate and the dead plate enable hydrogen and a reaction liquid to pass.

5. The method for preparing isophorone diamine by means of hydrogenation reduction of isophorone nitrile imine according to claim 1, wherein the supported alkaline cobalt-based catalyst comprises a carrier, an active component, and an alkaline component; the carrier includes one or more of alumina, titania, zirconium dioxide, and magnesia; the active component is Co; and the alkaline component includes an oxide of Mg, Ca, Na or K.

6. The method for preparing isophorone diamine by means of hydrogenation reduction of isophorone nitrile imine according to claim 5, wherein the active component has a mass fraction of 30% to 50%; and the alkaline component has a mass fraction of 0.1% to 5%.

7. The method for preparing isophorone diamine by means of hydrogenation reduction of isophorone nitrile imine according to claim 1, wherein isophorone nitrile imine, when added as a reaction material, has a mass fraction of 97% or more.

8. The method for preparing isophorone diamine by means of hydrogenation reduction of isophorone nitrile imine according to claim 1, wherein a molar ratio of hydrogen to isophorone nitrile imine during the hydrogenation reduction reaction is 5 to 100:1; and a space-time processing capacity of catalyst of the multistage bubble column reactor is 0.05 to 0.3 mol/(L*h).

9. The method for preparing isophorone diamine by means of hydrogenation reduction of isophorone nitrile imine according to claim 1, wherein a reaction temperature in the multistage bubble column reactor is 60° C. to 160° C., and the temperatures in adjacent stage reactors are the same or increase successively; and a reaction pressure in the multistage bubble column reactor is 3 to 10 MPa.

* * * * *